(12) United States Patent
Harada et al.

(10) Patent No.: US 11,706,379 B2
(45) Date of Patent: Jul. 18, 2023

(54) X-RAY IMAGING APPARATUS

(71) Applicant: Shimadzu Corporation, Kyoto (JP)

(72) Inventors: Daisuke Harada, Kyoto (JP); Takuma Niizaka, Kyoto (JP)

(73) Assignee: Shimadzu Corporation, Kyoto (JP)

(*) Notice: Subject to any disclaimer, the term of this patent is extended or adjusted under 35 U.S.C. 154(b) by 182 days.

(21) Appl. No.: 17/436,866

(22) PCT Filed: Mar. 14, 2019

(86) PCT No.: PCT/JP2019/010708
§ 371 (c)(1),
(2) Date: Sep. 7, 2021

(87) PCT Pub. No.: WO2020/183733
PCT Pub. Date: Sep. 17, 2020

(65) Prior Publication Data
US 2022/0166942 A1 May 26, 2022

(51) Int. Cl.
*H04N 5/32* (2023.01)
*G06T 5/50* (2006.01)

(52) U.S. Cl.
CPC .......... *H04N 5/32* (2013.01); *G06T 5/50* (2013.01); *G06T 2207/10124* (2013.01); *G06T 2207/20212* (2013.01)

(58) Field of Classification Search
None
See application file for complete search history.

(56) References Cited

U.S. PATENT DOCUMENTS

| 2005/0063611 A1 | 3/2005 | Toki et al. |
| 2017/0071554 A1* | 3/2017 | Fukuda ............... A61B 6/502 |
| 2017/0231589 A1* | 8/2017 | Fujii .................. A61B 6/032 |
| | | 378/20 |

FOREIGN PATENT DOCUMENTS

JP 2005-095328 A 4/2005

OTHER PUBLICATIONS

Written Opinion for PCT application PCT/JP2019/010708 dated May 28, 2019 by the International Search Authority submitted with a machine translation.

* cited by examiner

*Primary Examiner* — Edwin C Gunberg
(74) *Attorney, Agent, or Firm* — Muir Patent Law, PLLC

(57) ABSTRACT

In an X-ray imaging apparatus (100), an image processor (5b) is configured to apply a super-resolution process to a first region (A1) in each of acquired images (Ia), the first region including a subject (S), and to increase a number of pixels according to an increase in resolution in the first region by application of the super-resolution process thereto by a simpler process than the super-resolution process with respect to a second region (A2) other than the first region in each of the acquired images.

8 Claims, 6 Drawing Sheets

X-RAY IMAGING APPARATUS

TECHNICAL FIELD

The present invention relates to an X-ray imaging apparatus, and more particularly, it relates to an X-ray imaging apparatus that generates a high-resolved image having higher resolution than an acquired image by performing a super-resolution process to increase the resolution.

BACKGROUND ART

Conventionally, an X-ray imaging apparatus that generates a high-resolved image having higher resolution than an acquired image by performing a super-resolution process to increase the resolution is known (see Patent Document 1, for example).

Patent Document 1 discloses an X-ray imaging apparatus including a data storage that stores a plurality of acquired projection data (acquired images) related to a subject and a reconstruction processor that generates a reconstructed image obtained by reconstructing the plurality of projection data. The X-ray imaging apparatus disclosed in Patent Document 1 includes an input for a user to manually specify a range on the reconstructed image to which a super-resolution process is applied, and a super-resolution processor that performs the super-resolution process by limiting to the specified range for the super-resolution process. Then, the image on which the super-resolution process has been manually performed is treated as one image (high-resolved image) and displayed.

PRIOR ART

Patent Document

Patent Document 1: Japanese Patent Laid-Open No. 2005-095328

SUMMARY OF THE INVENTION

Problem to be Solved by the Invention

Although in a conventional X-ray imaging apparatus as described in Patent Document 1, the time taken to generate a high-resolved image can be shortened by limiting the range to which the super-resolution process is applied, the range treated as one image (high-resolved image) is limited to the range that has undergone the super-resolution process, and thus the range treated as one image (high-resolved image) disadvantageously becomes smaller than an original acquired image.

The present invention is intended to solve the above problem. The present invention aims to provide an X-ray imaging apparatus capable of generating a high-resolved image while significantly reducing or preventing an increase in the calculation time taken to generate the high-resolved image and significantly reducing or preventing a decrease in a range of the image treated as one image.

Means for Solving the Problem

In order to attain the aforementioned object, an X-ray imaging apparatus according to an aspect of the present invention includes an X-ray source, a detector configured to detect X-rays radiated from the X-ray source at a plurality of detection positions translated by a movement amount smaller than a pixel size of the detector from each other, and an image processor configured to generate a plurality of acquired images based on the X-rays detected at the plurality of detection positions, respectively, the image processor being configured to generate a high-resolved image having higher resolution than the plurality of acquired images by performing a super-resolution process to increase resolution based on the plurality of acquired images. The image processor is configured to apply the super-resolution process to a first region in each of the acquired images, the first region including a subject, and to increase a number of pixels according to an increase in resolution in the first region by application of the super-resolution process thereto by a simpler process than the super-resolution process with respect to a second region other than the first region in each of the acquired images.

In the X-ray imaging apparatus according to this aspect of the present invention, as described above, the image processor applies the super-resolution process to the first region in each of the acquired images, the first region including the subject, and increases the number of pixels according to an increase in the resolution in the first region by the application of the super-resolution process thereto by the simpler process than the super-resolution process with respect to the second region other than the first region in each of the acquired images. Accordingly, the resolution of the second region to which the super-resolution process is not applied can be increased according to the increase in the resolution of the first region to which the super-resolution process is applied, and thus the first region and the second region can be treated as one image even when the super-resolution process is applied only to the first region. Furthermore, the image processor applies the super-resolution process to the first region and increases the number of pixels by the simpler process than the super-resolution process with respect to the second region, and thus the calculation time can be reliably shortened as compared with a case in which the super-resolution process is performed on the entire acquired image. Consequently, it is possible to generate the high-resolved image while significantly reducing or preventing an increase in the calculation time taken to generate the high-resolved image and significantly reducing or preventing a decrease in a range of the image treated as one image.

In the aforementioned X-ray imaging apparatus according to this aspect, the image processor is preferably configured to increase the number of pixels by an increase rate equal to an increase rate of the number of pixels due to the increase in the resolution in the first region by the application of the super-resolution process thereto with respect to the second region in each of the acquired images to which the super-resolution process is not applied. Accordingly, the sizes of the pixels in the first region and the second region are the same as each other, and thus the super-resolution processed image including the first region and the second region can be easily treated as one image (high-resolved image).

In this case, the image processor is preferably configured to increase the number of pixels by the increase rate by interpolating between the pixels in the second region by an image process. Accordingly, it is possible to easily interpolate between the pixels by the pixel interpolation process, which is a simpler process than the super-resolution process, and thus the number of pixels can be easily increased by the above increase rate.

In the aforementioned X-ray imaging apparatus according to this aspect, the image processor is preferably configured to apply the super-resolution process using successive approximation calculation to the first region. The super-resolution process using the successive approximation calculation has a particularly long calculation time in the super-resolution process method. That is, even when the super-resolution process using the successive approximation calculation that requires a relatively long calculation time is performed, with the configuration of the X-ray imaging apparatus according to this aspect, it is possible to generate the high-resolved image while significantly reducing or preventing an increase in the calculation time taken to generate the high-resolved image and significantly reducing or preventing a decrease in a range of the image treated as one image.

In the aforementioned X-ray imaging apparatus according to this aspect, the image processor is preferably configured to acquire the first region by an image process based on image data of the acquired images. Accordingly, the image processor can automatically acquire the first region by the image process, and thus the image processor can apply the super-resolution process to the first region without a user manually setting the first region.

In this case, the image processor is preferably configured to acquire the first region based on magnitude of a luminance value or magnitude of a spatial frequency in each of the acquired images. A region in the image in which the subject exists has a larger (or smaller) luminance value than a region in the image in which the subject does not exist. Furthermore, the luminance value and the spatial frequency change significantly at a boundary between the region in the image in which the subject exists and the region in the image in which the subject does not exist. Therefore, with the configuration described above, the image processor can easily acquire the first region based on the image data of the acquired images. The "spatial frequency" indicates the number of structural repetitions included in the unit length. For example, a high spatial frequency in the image indicates that a sudden change such as an edge has occurred.

In the aforementioned X-ray imaging apparatus according to this aspect, the detector is preferably configured to detect, from a plurality of directions, the X-rays radiated from the X-ray source while rotating about a rotation axis, the image processor is preferably configured to generate a plurality of two-dimensional acquired images based on the X-rays detected from the plurality of directions, respectively, and to generate a three-dimensional reconstructed image obtained by reconstructing the plurality of two-dimensional acquired images, and the first region is preferably set by a user based on data of the three-dimensional reconstructed image. The three-dimensional reconstructed image obtained by reconstructing the plurality of two-dimensional acquired images is configured as three-dimensional voxel data, and thus arbitrary cross-sections can be cut out from the three-dimensional reconstructed image. Therefore, with the configuration described above, the first region for the three-dimensional voxel data can be set by setting regions for at least two images viewed in the different directions, which are obtained by cutting out arbitrary cross-sections from the three-dimensional reconstructed image. Then, the first region for a plurality of pieces of two-dimensional pixel data can be set by converting the three-dimensional voxel data into the plurality of pieces of two-dimensional pixel data. That is, the first region can be set for many of the plurality of two-dimensional acquired images used to generate the three-dimensional reconstructed image simply by setting the first region for at least the two images. Consequently, as compared with a case in which the first region is set one by one for many of the two-dimensional acquired images used to generate the reconstructed image, the operation load for the user to set the first region can be significantly reduced or prevented. In general, many (several hundred to several thousand, for example) two-dimensional acquired images are used to generate the three-dimensional reconstructed image.

In this case, the image processor is preferably configured to set, as the first region, a region in the three-dimensional reconstructed image corresponding to regions set by the user in at least two two-dimensional sectional images viewed in different directions, the at least two two-dimensional sectional images being obtained by cutting out arbitrary cross-sections from the three-dimensional reconstructed image, and to set the first region in the plurality of two-dimensional acquired images by converting the three-dimensional reconstructed image in which the first region has been set into the plurality of two-dimensional acquired images. Accordingly, the first region can be reliably set for many of the two-dimensional acquired images simply by setting the first region for at least the two images, and thus as compared with a case in which the first region is set one by one for many of the two-dimensional acquired images, the operation load for the user to set the first region can be reliably significantly reduced or prevented.

Effect of the Invention

According to the present invention, as described above, it is possible to generate a high-resolved image while significantly reducing or preventing an increase in the calculation time taken to generate the high-resolved image and significantly reducing or preventing a decrease in a range of the image treated as one image.

MODES FOR CARRYING OUT THE INVENTION

Embodiments embodying the present invention are hereinafter described on the basis of the drawings.

The configuration of an X-ray imaging apparatus 100 according to a first embodiment of the present invention is now described with reference to FIGS. 1 to 7.

Figure 1:
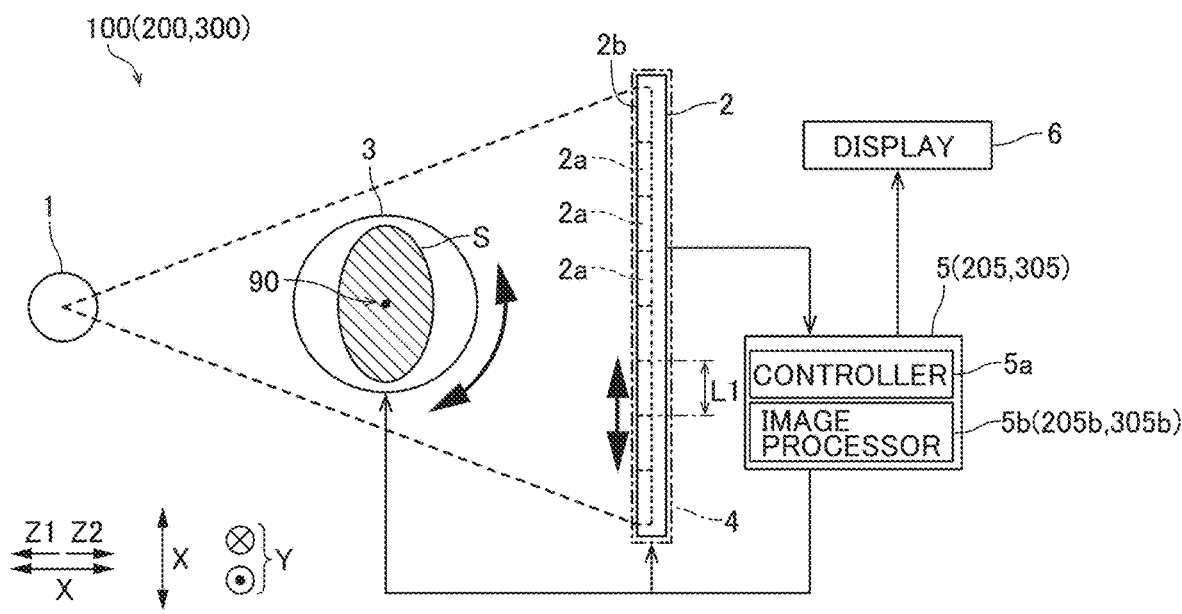
FIG. 1 is a diagram showing the overall configuration of an X-ray imaging apparatus according to a first embodiment of the present invention as viewed in a Y direction.

As shown in FIG. 1, the X-ray imaging apparatus 100 includes an X-ray source 1, a detector 2, a rotating stage 3, a detector moving mechanism 4, a processing unit 5, and a display 6.

In the X-ray imaging apparatus 100, the X-ray source 1, the rotating stage 3, and the detector 2 are arranged side by side in this order in a direction (Z direction) connecting the X-ray source 1 to the detector 2. In this description, a direction from the X-ray source 1 toward the detector 2 is defined as a Z2 direction, and the opposite direction is defined as a Z1 direction. A direction in which the rotating stage 3 translates in an in-plane direction orthogonal to the Z direction is defined as a Y direction. A direction orthogonal to the Z direction and the Y direction is defined as an X direction.

The X-ray source 1 is an X-ray generator capable of generating X-rays by a high voltage applied thereto. The X-ray source 1 radiates the generated X-rays in the Z2 direction.

The detector 2 detects the X-rays radiated from the X-ray source 1 and converts the detected X-rays into electric signals. The detector 2 has a detection surface 2b including a plurality of detection elements 2a arranged side by side in a matrix in the X direction and the Y direction at a predetermined period L1. The detector 2 includes a plurality of conversion elements (not shown) that are arranged so as to correspond to the plurality of detection elements 2a, respectively, and convert the detected X-rays into electric signals. The detector 2 is a flat panel detector (FPD), for example. The detection signals (electric signals) converted by the detector 2 are transmitted to an image processor 5b (described below) of the processing unit 5.

Figure 2:
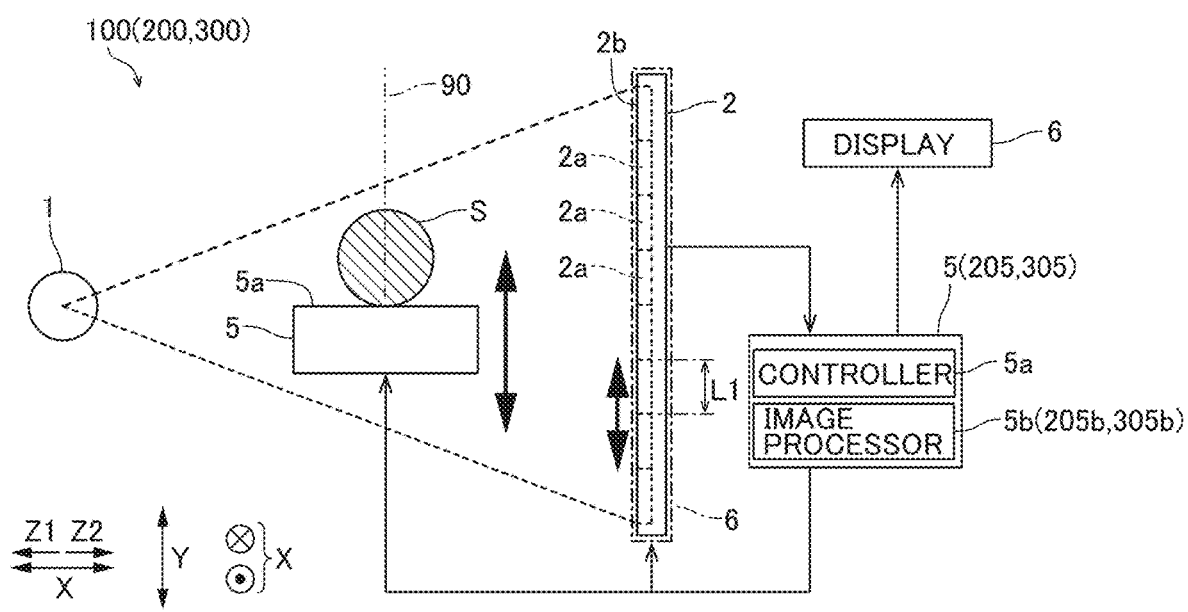
FIG. 2 is a diagram showing the overall configuration of the X-ray imaging apparatus according to the first embodiment of the present invention as viewed in an X direction.

The rotating stage 3 has a placement surface 3a (see FIG. 2) on which a subject S is placed. The rotating stage 3 can rotate 360 degrees about a rotation axis 90 along the Y direction in an XZ plane. As shown in FIG. 2, the rotating stage 3 can translate in the Y direction. Thus, in the first embodiment, the detector 2 can perform tomographic imaging by alternately repeating detection operation to detect X-rays radiated from the X-ray source 1 from a plurality of directions (in the XZ plane) while rotating with the Y direction as a rotation axis and translation in the Y direction. That is, the X-ray imaging apparatus 100 is an imaging apparatus capable of performing so-called non-helical scan-type tomographic imaging.

Figure 3:
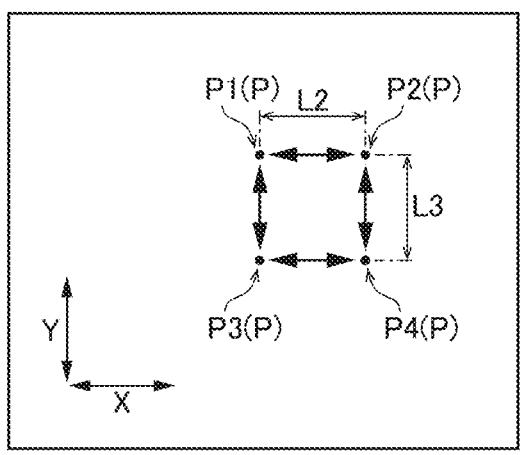
FIG. 3 is a diagram illustrating detection positions of X-rays in the X-ray imaging apparatus according to the first embodiment of the present invention.

As shown in FIGS. 1 and 2, the detector moving mechanism 4 can move the detector 2 in the X direction and the Y direction by a movement amount smaller than the detection element 2a. Thus, as shown in FIG. 3, the detector moving mechanism 4 can move the detector 2 between a first position P1, a second position P2, a third position P3, and a fourth position P4. The second position P2 is a position translated from the first position P1 by a distance L2 in the X direction. The third position P3 is a position translated from the first position P1 by a distance L3 in the Y direction. The fourth position P4 is a position translated to the same side as the third position P3 translated from the first position P1 by the distance L3 in the Y direction. The distance L2 and the distance L3 are distances smaller than the size (the period in which the detection elements 2a are aligned) L1 of one detection element 2a in the X direction and the Y direction, respectively. That is, in the X-ray imaging apparatus 100, the detector 2 can detect X-rays radiated from the X-ray source 1 at a plurality of detection positions P translated by a movement amount smaller than one pixel Ea (E) (see FIG. 5) from each other.

The processing unit 5 includes a controller 5a and the image processor 5b.

The controller 5a controls the operation of the rotating stage 3 and the detector moving mechanism 4. The controller 5a includes a central processing unit (CPU), a read-only memory (ROM), and a random access memory (RAM), for example.

The image processor 5b generates a fluoroscopic X-ray image Ia (see FIG. 4) based on the detection signals transmitted from the detector 2. The image processor 5b includes a processor such as a graphics processing unit (GPU) or a field-programmable gate array (FPGA) configured for image processing, for example. Data of each pixel Ea (E) (see FIG. 5) in the fluoroscopic X-ray image Ia (see FIG. 4) corresponds to an X-ray dose detected by each detection element 2a of the detector 2. The fluoroscopic X-ray image Ia is an example of an "acquired image" in the claims.

The image processor 5b generates a plurality of fluoroscopic X-ray images Ia based on the X-rays detected at the plurality of detection positions P, respectively, and generates a high-resolved image 50 (see FIG. 5) having higher resolution than the plurality of fluoroscopic X-ray images Ia based on the plurality of fluoroscopic X-ray images Ia. The image processor 5b generates the high-resolved image 50 by performing a super-resolution process to increase the resolution based on the plurality of fluoroscopic X-ray images Ia.

Figure 4:
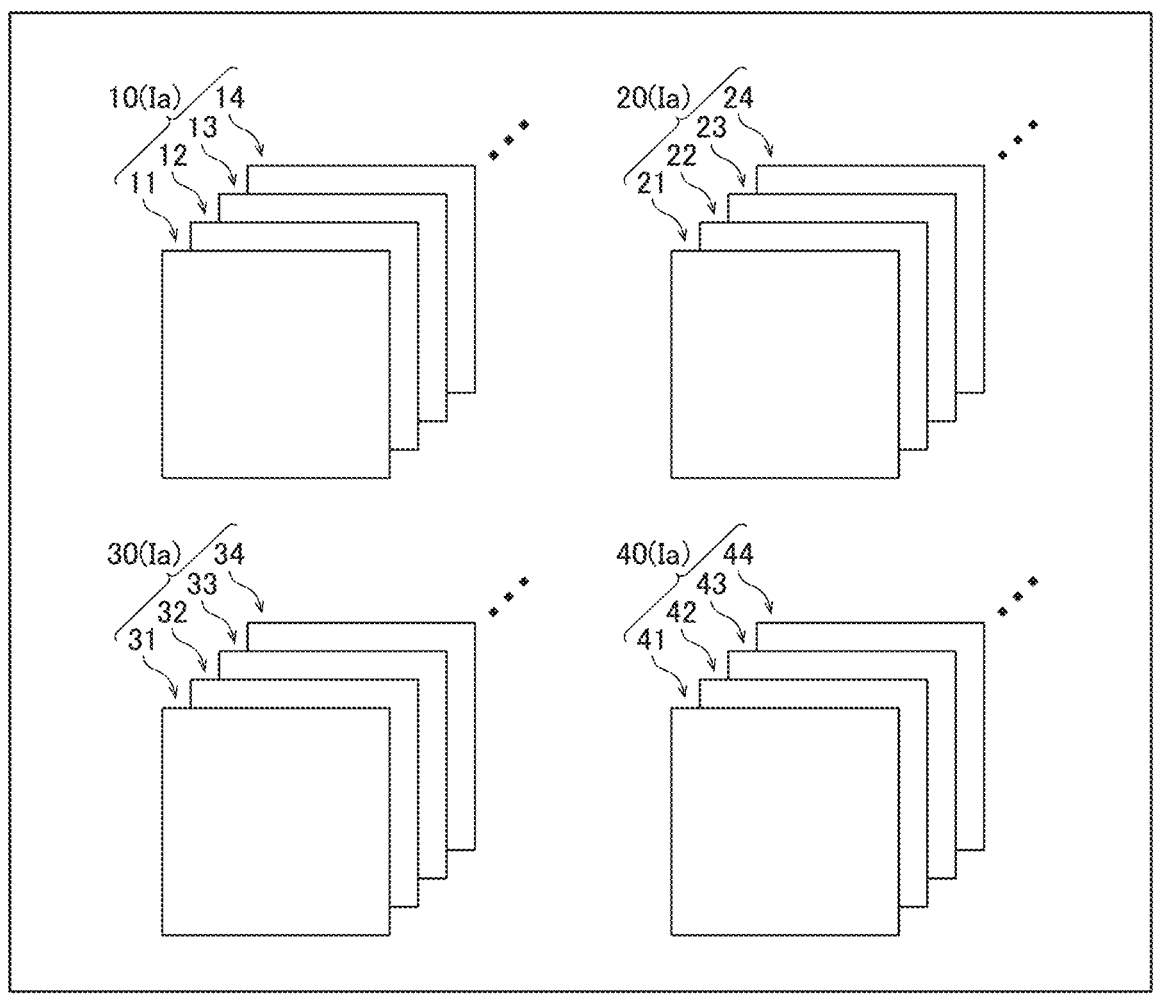
FIG. 4 is a diagram illustrating fluoroscopic X-ray images captured by the X-ray imaging apparatus according to the first embodiment of the present invention.

Specifically, as shown in FIG. 4, the image processor 5b generates, as the fluoroscopic X-ray images Ia, fluoroscopic X-ray images 10, 20, 30, and 40 based on the X-rays detected at the first position P1, the second position P2, the third position P3, and the fourth position P4, respectively. The fluoroscopic X-ray image 10 includes fluoroscopic X-ray images 11, 12, 13, 14, . . . , in which at least one of the imaging directions in the XZ plane or the imaging positions in the Y direction are different from each other due to the rotating stage 3. The fluoroscopic X-ray image 20 includes fluoroscopic X-ray images 21, 22, 23, 24, . . . , in which at least one of the imaging directions in the XZ plane or the imaging positions in the Y direction are different from each other due to the operation of the rotating stage 3. The fluoroscopic X-ray image 30 includes fluoroscopic X-ray images 31, 32, 33, 34, . . . , in which at least one of the imaging directions in the XZ plane or the imaging positions in the Y direction are different from each other due to the operation of the rotating stage 3. The fluoroscopic X-ray image 40 includes fluoroscopic X-ray images 41, 42, 43, 44, . . . , in which at least one of the imaging directions in the XZ plane or the imaging positions in the Y direction are different from each other due to the operation of the rotating stage 3.

Figure 5:
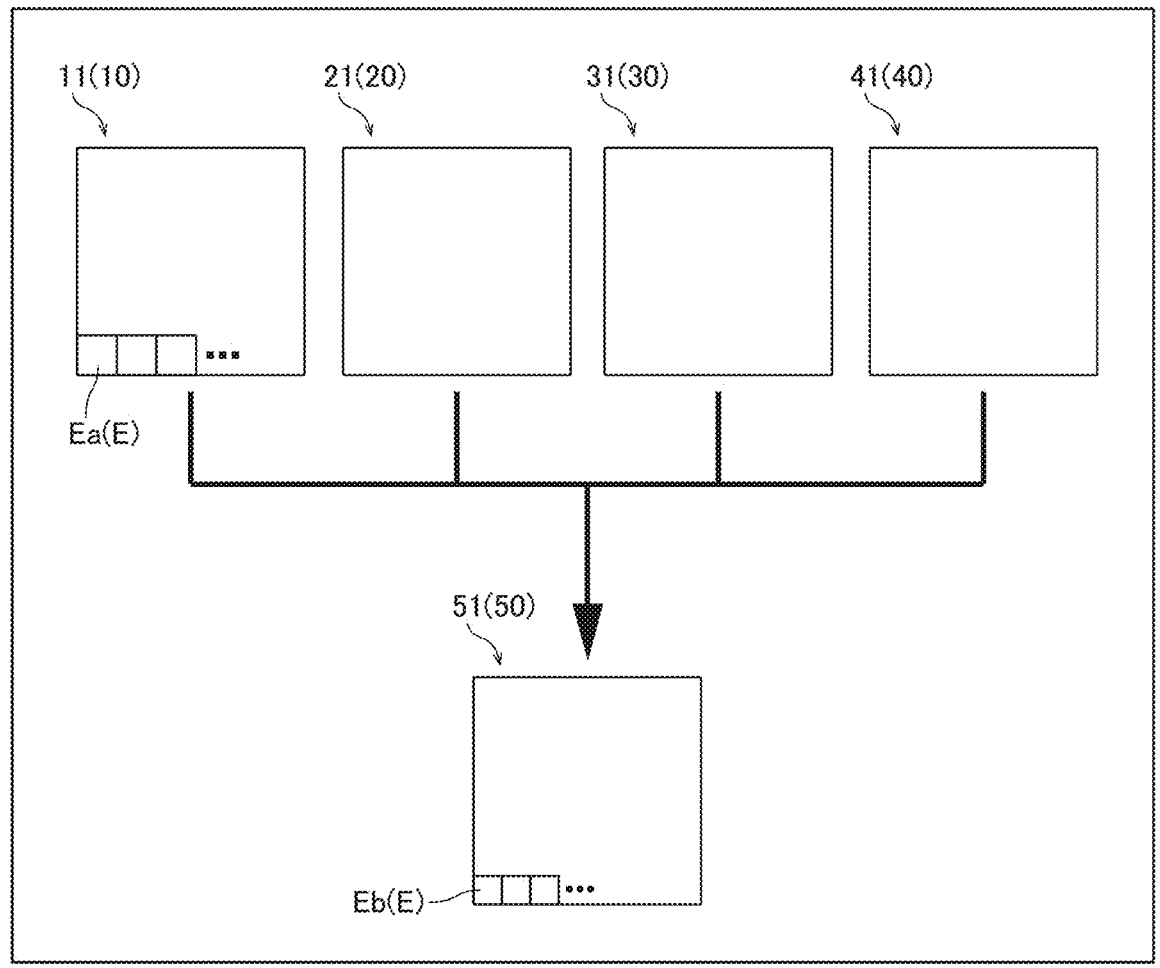
FIG. 5 is a diagram illustrating generation of a high-resolved image in the X-ray imaging apparatus according to the first embodiment of the present invention.

As shown in FIG. 5, the image processor 5b generates a high-resolved image 50 having higher resolution than the fluoroscopic X-ray images 10, 20, 30, and 40 by performing the super-resolution process on the fluoroscopic X-ray images 10, 20, 30, and 40. The high-resolved image 50 that has undergone the super-resolution process has pixels Eb (E) smaller than the sizes of pixels Ea (E) of the fluoroscopic X-ray images 10, 20, 30, and 40. In the X-ray imaging apparatus 200, the image processor 5b performs the super-resolution process by an optimization method using successive approximation calculation. The successive approximation calculation indicates an iterative backward projection (IBP) method, for example.

Figure 6:
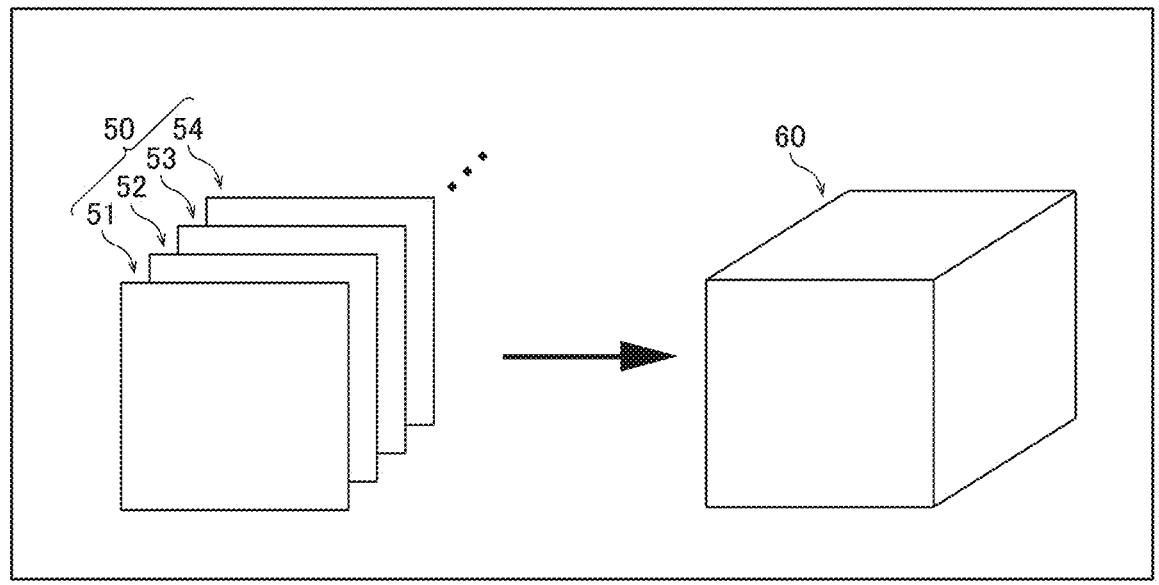
FIG. 6 is a diagram illustrating generation of a reconstructed image in the X-ray imaging apparatus according to the first embodiment of the present invention.

As shown in FIG. 6, the image processor 5b generates a three-dimensional reconstructed image 60 obtained by reconstructing a plurality of two-dimensional high-resolved images 50 (51, 52, 53, 54, . . . ). Each of the high-resolved images 51, 52, 53, 54, . . . has (two-dimensional) pixel data. The high-resolved image 51 is generated by performing the super-resolution process on the fluoroscopic X-ray images 11, 21, 31, and 41. The high-resolved image 52 is generated by performing the super-resolution process on the fluoroscopic X-ray images 12, 22, 32, and 42. The high-resolved image 53 is generated by performing the super-resolution process on the fluoroscopic X-ray images 13, 23, 33, and 43. The high-resolved image 54 is generated by performing the super-resolution process on the fluoroscopic X-ray images 14, 24, 34, and 44. The reconstructed image 60 has (three-dimensional) voxel data. In the X-ray imaging apparatus 100, many (several hundred to several thousand, for example) two-dimensional high-resolved images 50 are reconstructed to generate a three-dimensional reconstructed image 60.

The display 6 is configured to display images (such as the fluoroscopic X-ray image Ia, the high-resolved image 50, and the reconstructed image 60) generated by the image processor 5b. The display 6 includes a monitor such as a liquid crystal display, for example.

Figure 7:
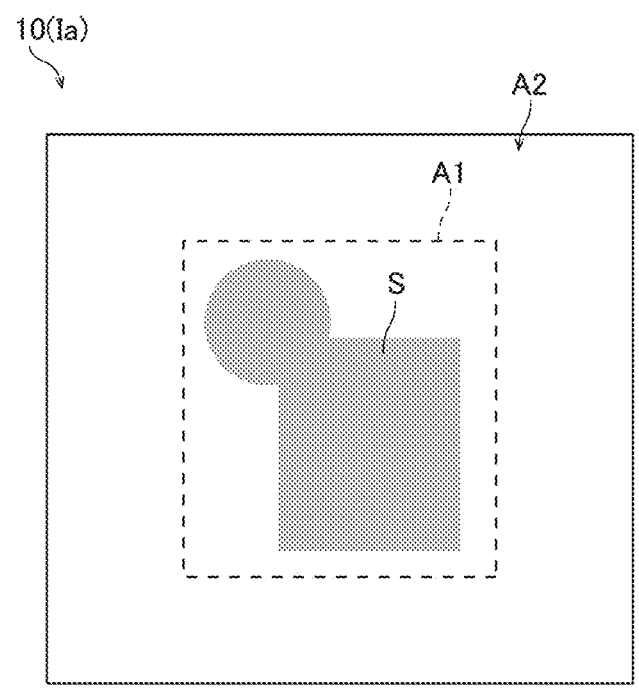
FIG. 7 is a diagram illustrating setting of a first region in the X-ray imaging apparatus according to the first embodiment of the present invention.

As shown in FIG. 7, in the first embodiment, the image processor 5b applies the super-resolution process to a first region A1 (a rectangular region, for example) of the fluoroscopic X-ray image Ia in which the subject S exists. Furthermore, the image processor 5b increases the number of pixels according to an increase in the resolution in the first region A1 by the application of the super-resolution process thereto by a simpler process than the super-resolution process with respect to a second region A2 (a frame-shaped region, for example) other than the first region A1 in the fluoroscopic X-ray image Ia.

Specifically, the image processor 5b increases the number of pixels with respect to the second region A2 by an increase rate equal to the increase rate of the number of pixels due to the increase in the resolution in the first region A1 by the application of the super-resolution process thereto. Furthermore, the image processor 5b increases the number of pixels by the above increase rate by interpolating between pixels E in the second region A2 by an image process.

More specifically, in the X-ray imaging apparatus 100, a user selects the first region A1 to which the super-resolution process is applied in the fluoroscopic X-ray image Ia displayed on the display 6 (see FIG. 1) via an operation unit (not shown). The image processor 6b performs the super-resolution process on the first region A1 in the fluoroscopic X-ray image Ia selected by the user. Furthermore, the image processor 6b performs a pixel E interpolation process on the first region A1 to increase the number of pixels by an amount increased in the first region A1 by the super-resolution process with respect to the second region A2 other than the first region A1 in the fluoroscopic X-ray image Ia. For example, when the number of pixels in the first region A1 is quadrupled, the pixel E interpolation process is performed such that the number of pixels in the second region A2 is quadrupled. The pixel E interpolation process is preferably a process having a relatively low calculation load, such as nearest neighbor interpolation or bilinear interpolation.

Advantages of First Embodiment

In the first embodiment, the following advantages are obtained.

In the first embodiment, as described above, the image processor 5b is configured to apply the super-resolution process to the first region A1 in the fluoroscopic X-ray image Ia including the subject S. Furthermore, the image processor 5b is configured to increase the number of pixels according to an increase in the resolution in the first region A1 by the application of the super-resolution process thereto by the simpler process than the super-resolution process with respect to the second region A2 other than the first region A1 in the fluoroscopic X-ray image Ia. Accordingly, the resolution of the second region A2 to which the super-resolution process is not applied can be increased according to the increase in the resolution of the first region A1 to which the super-resolution process is applied, and thus the first region A1 and the second region A2 can be treated as one image even when the super-resolution process is applied only to the first region A1. Furthermore, the image processor 5b applies the super-resolution process to the first region A1 and increases the number of pixels by the simpler process than the super-resolution process with respect to the second region A2, and thus the calculation time can be reliably shortened as compared with a case in which the super-resolution process is performed on the entire fluoroscopic X-ray image Ia. Consequently, it is possible to generate the high-resolved image 50 while significantly reducing or preventing an increase in the calculation time taken to generate the high-resolved image 50 and significantly reducing or preventing a decrease in a range of the image treated as one image.

In the first embodiment, as described above, the image processor 5b is configured to increase the number of pixels by the increase rate equal to the increase rate of the number of pixels due to the increase in the resolution in the first region A1 by the application of the super-resolution process thereto with respect to the second region A2 in the fluoroscopic X-ray image Ia to which the super-resolution process is not applied. Accordingly, the sizes of the pixels E in the first region A1 and the second region A2 are the same as each other, and thus the super-resolution processed image including the first region A1 and the second region A2 can be easily treated as one image (high-resolved image 50).

In the first embodiment, as described above, the image processor 5b is configured to increase the number of pixels by the above increase rate by interpolating between the pixels E in the second region A2 by the image process. Accordingly, it is possible to easily interpolate between the pixels E by the pixel E interpolation process, which is a simpler process than the super-resolution process, and thus the number of pixels can be easily increased by the above increase rate.

In the first embodiment, as described above, the image processor 5b is configured to apply the super-resolution process using the successive approximation calculation to the first region A1. Accordingly, even when the super-resolution process using the successive approximation calculation that requires a relatively long calculation time is performed, it is possible to generate the high-resolved image 50 while significantly reducing or preventing an increase in the calculation time taken to generate the high-resolved image 50 and significantly reducing or preventing a decrease in a range of the image treated as one image.

Second Embodiment

Figure 8:
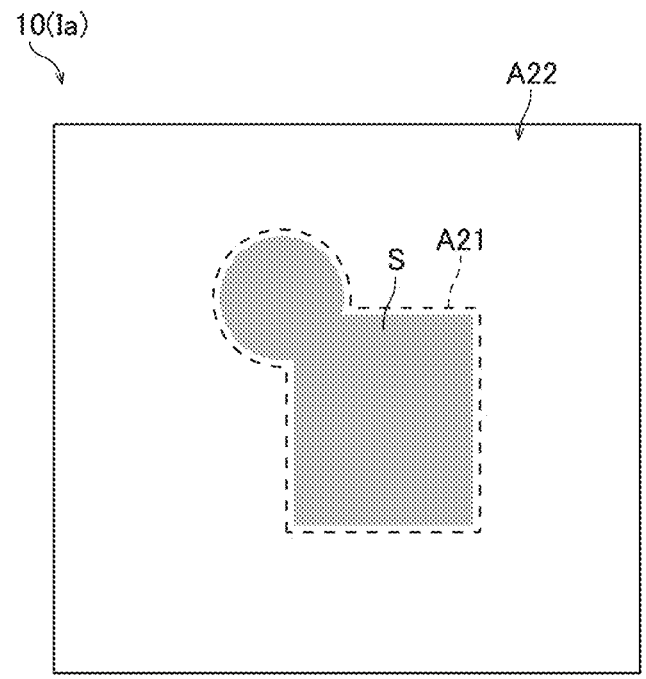
FIG. 8 is a diagram illustrating setting of a first region in an X-ray imaging apparatus according to a second embodiment of the present invention.

A second embodiment is now described with reference to FIGS. 1 and 8. In this second embodiment, an example is described in which an image processor 6b automatically sets a first region A1, unlike the first embodiment in which the user selects the first region A1 to which the super-resolution process is applied. The same or similar configurations as those of the first embodiment are denoted by the same reference numerals in the figures.

As shown in FIG. 1, an X-ray imaging apparatus 200 according to the second embodiment of the present invention includes a processing unit 205. The processing unit 205 includes the image processor 205b.

As shown in FIG. 2, in the second embodiment, the image processor 205b is configured to acquire the first region A21 by an image process based on image data of a fluoroscopic X-ray image Ia. Specifically, the image processor 205b is configured to acquire the first region A21 based on the magnitude of the luminance value in the fluoroscopic X-ray image Ia.

Specifically, the image processor 205b determines whether or not a subject S exists based on either the magnitude of the luminance value or a change in the magnitude of the luminance value in the fluoroscopic X-ray image Ia, and acquires the first region A21. That is, a region in which the subject S exists has a larger luminance value than a region in which the subject S does not exist, and thus the image processor 205b determines whether or not the subject S exists by searching for a region of the fluoroscopic X-ray image Ia in which pixels E having a relatively large luminance value are continuous by the image process. When the subject S is reflected relatively clearly, a boundary between the region of the fluoroscopic X-ray image Ia in which the subject S exists and the region of the fluoroscopic X-ray image Ia in which the subject S does not exist appears relatively clearly in the magnitude of the luminance value (a change in the magnitude of the luminance value is large), and thus the image processor 205b determines whether or not the subject S exists by edge detection by the image process. The first region A21 is a region (i.e., a region slightly larger than the subject S) obtained by surrounding the subject S with pixels E separated by several pixels E from the edge of the subject S.

The remaining configurations of the X-ray imaging apparatus 200 according to the second embodiment are similar to those according to the first embodiment.

Advantages of Second Embodiment

In the second embodiment, the following advantages are obtained.

In the second embodiment, as described above, the image processor 205b is configured to acquire the first region A21 by the image process based on the image data of the fluoroscopic X-ray image Ia. Accordingly, the image processor 205b can automatically acquire the first region A21 by the image process, and thus the image processor 205b can apply the super-resolution process to the first region A21 without the user manually setting the first region A21.

In the second embodiment, as described above, the image processor 205b is configured to acquire the first region A21 based on the magnitude of the luminance value in the fluoroscopic X-ray image Ia. Accordingly, the image processor 205b can easily acquire the first region A21 based on the image data of the fluoroscopic X-ray image Ia.

The remaining advantages of the second embodiment are similar to those of the first embodiment.

Third Embodiment

A third embodiment is now described with reference to FIGS. 1 and 9 to 11. In this third embodiment, an example is described in which a user selects a first region A31 based on data of a reconstructed image 360 (see FIG. 9) displayed on a display 6, unlike the first embodiment in which the user selects the first region A1 in the fluoroscopic X-ray image Ia displayed on the display 6 (see FIG. 1). The same or similar configurations as those of the first embodiment are denoted by the same reference numerals in the figures.

As shown in FIG. 1, an X-ray imaging apparatus 300 according to the third embodiment of the present invention includes a processing unit 305. The processing unit 305 includes an image processor 305b.

Figure 9:
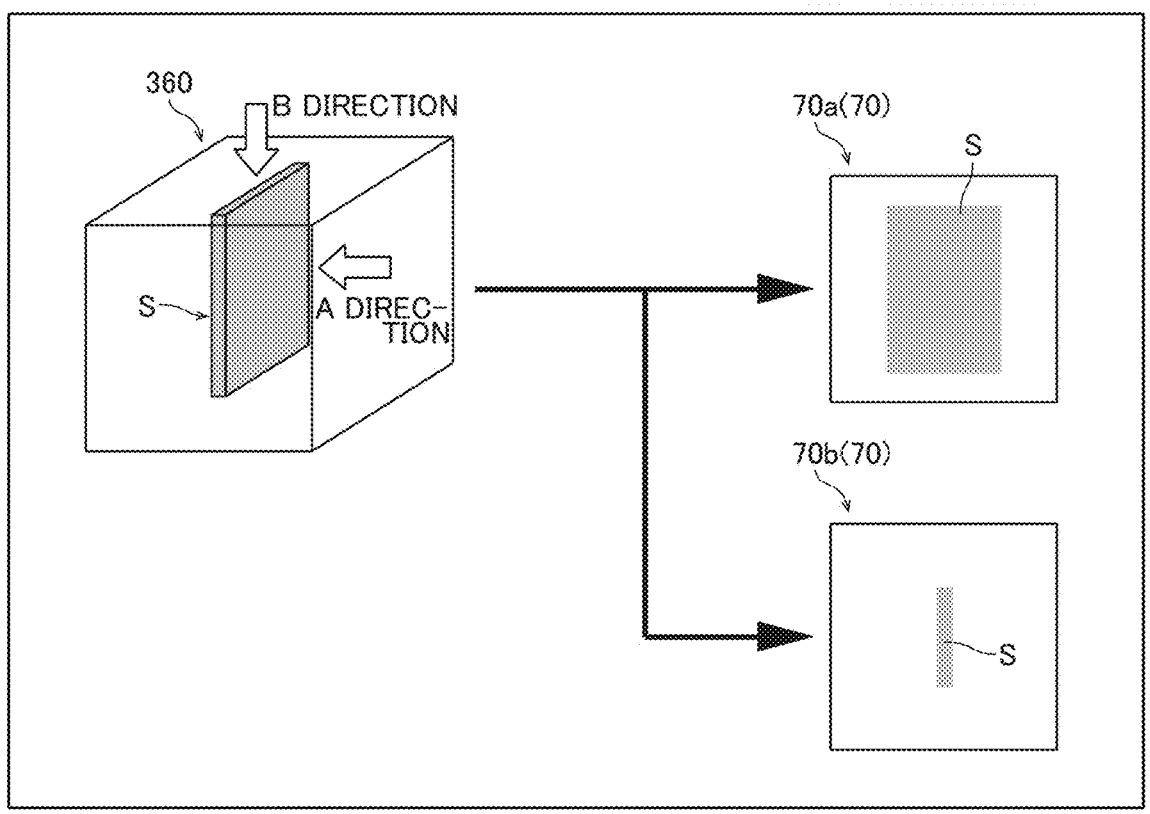
FIG. 9 is a diagram illustrating sectional images cut out from a reconstructed image in an X-ray imaging apparatus according to a third embodiment of the present invention.

As shown in FIG. 9, in the third embodiment, the image processor 305b sets the first region A31 (see FIG. 10) based on regions A31a (see FIG. 10) and A31b (see FIG. 10) set by the user based on the data of the three-dimensional reconstructed image 360. Specifically, the image processor 305b sets, as the first region A31, a region in the three-dimensional reconstructed image 360 corresponding to the regions A31a and A31b set by the user in two two-dimensional sectional images 70 viewed in different directions, which are obtained by cutting out arbitrary cross-sections from the three-dimensional reconstructed image 360. Then, the image processor 305b converts the three-dimensional reconstructed image 360 in which the first region A31 has been set into a plurality of two-dimensional fluoroscopic X-ray images Ia to set the first region A31 in the plurality of two-dimensional fluoroscopic X-ray images Ia. FIG. 9 shows an example in which a subject S has a plate shape.

Specifically, the image processor 305b generates the three-dimensional reconstructed image 360 obtained by reconstructing a plurality of two-dimensional fluoroscopic X-ray images Ia before performing a super-resolution process. The plurality of two-dimensional fluoroscopic X-ray images Ia are a plurality of fluoroscopic X-ray images 10 (11, 12, 13, 14, . . . ), for example.

In the X-ray imaging apparatus 300, the user selects arbitrary cross-sections in the reconstructed image 360 displayed on the display 6 (see FIG. 1) via an operation unit (not shown). The image processor 305b generates the sectional images 70 obtained by cutting out the cross-sections selected by the user, and displays the generated sectional images 70 on the display 6 (see FIG. 1). In FIG. 9, in the reconstructed image 360, as the sectional images 70, a sectional image 70a obtained by cutting out a cross-section viewed in an A direction and a sectional image 70b obtained by cutting out a cross-section viewed in a B direction are shown.

Figure 10:
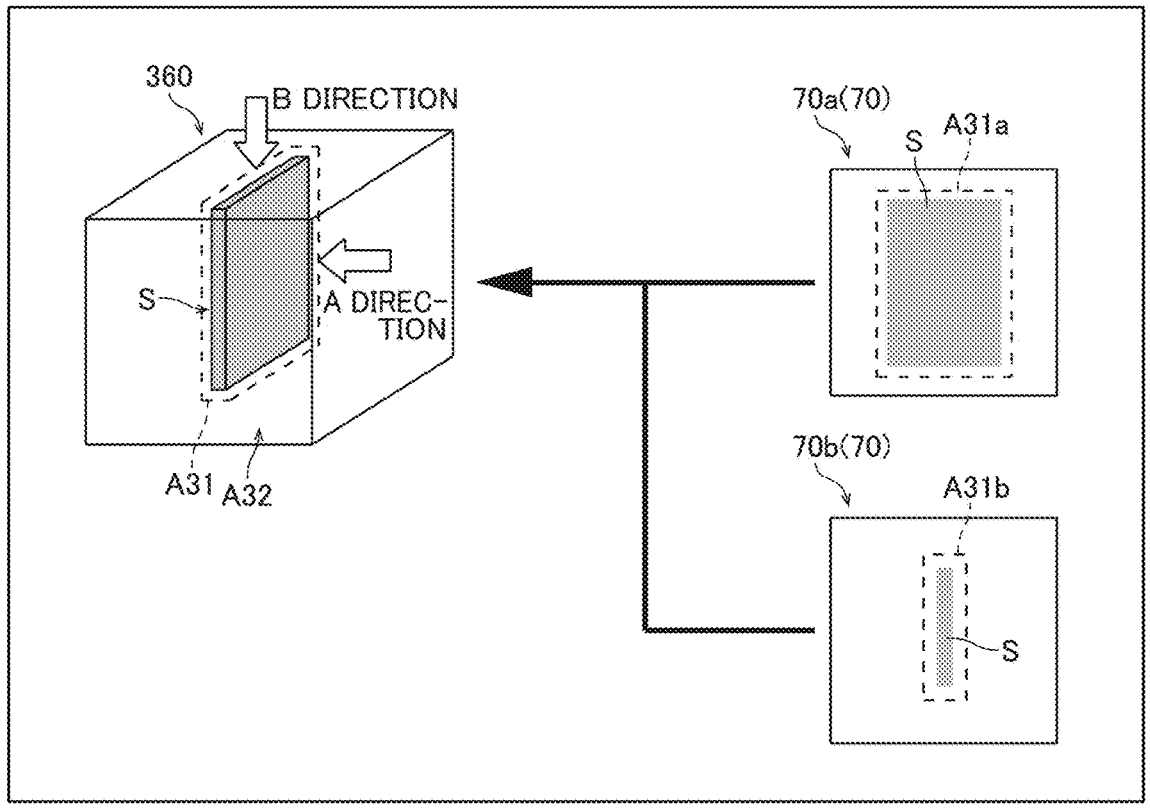
FIG. 10 is a diagram illustrating setting of a first region in the X-ray imaging apparatus according to the third embodiment of the present invention.

As shown in FIG. 10, the user selects the regions A31a and A31b in the sectional images 70a and 70b displayed on the display 6 (see FIG. 1) via the operation unit (not shown), respectively. The image processor 305b sets the first region A31 in the reconstructed image 360 based on the regions A31a and A31b selected in the sectional images 70a and 70b.

Figure 11:
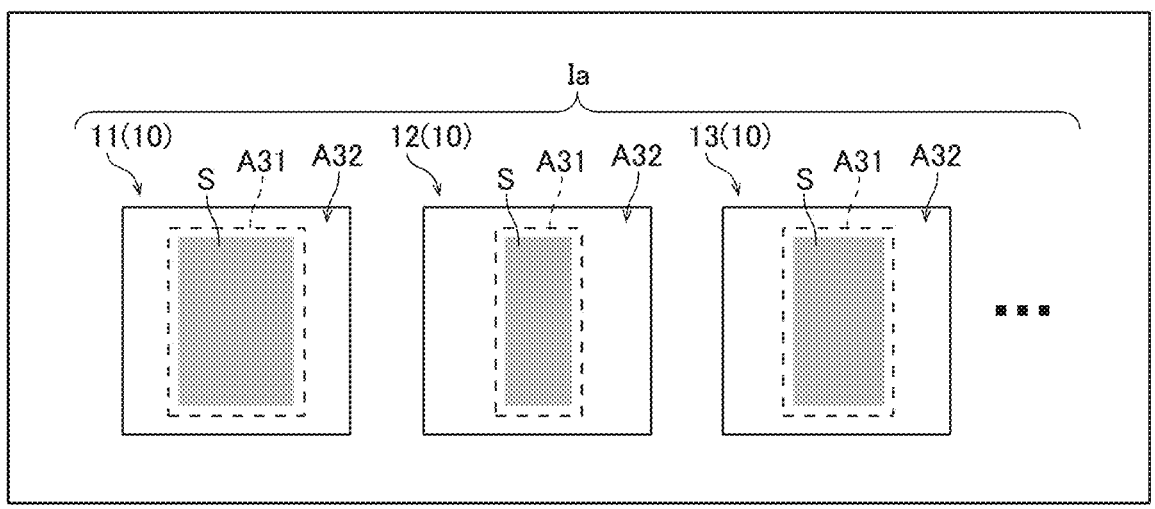
FIG. 11 is a diagram illustrating fluoroscopic X-ray images with the set first region in the X-ray imaging apparatus according to the third embodiment of the present invention.

As shown in FIG. 11, the image processor 305b reflects the first region A31 of the three-dimensional reconstructed image 360 in the plurality of two-dimensional fluoroscopic X-ray images Ia used for reconstruction of the reconstructed image 360 (converts three-dimensional voxel data to a plurality of two-dimensional pixel data). Furthermore, the image processor 305b sets a region other than the first region A31 as a second region A32 in the fluoroscopic X-ray image Ia. Thus, the first region A31 and the second region A32 are set for the plurality of two-dimensional fluoroscopic X-ray images Ia.

As shown in FIG. 9, the sectional image 70a obtained by cutting out the cross-section viewed in the A direction has a relatively large area of the subject S therein, and the sectional image 70b obtained by cutting out the cross-section viewed in the B direction has a relatively small area of the subject S therein. Thus, the first region A31 can be appropriately set by varying a range that undergoes the super-resolution process in the images viewed in various directions, and thus the calculation time taken to generate the high-resolved image 50 can be effectively shortened.

The remaining configurations of the X-ray imaging apparatus 300 according to the third embodiment are similar to those according to the first embodiment.

Advantages of Third Embodiment

In the third embodiment, the following advantages are obtained.

In the third embodiment, as described above, a detector 2 is configured to detect, from a plurality of directions, X-rays radiated from an X-ray source 1 while rotating about a rotation axis 90. The image processor 305b is configured to generate the plurality of two-dimensional fluoroscopic X-ray images Ia based on the X-rays detected from the plurality of directions, respectively, and generate the three-dimensional reconstructed image 360 obtained by reconstructing the plurality of two-dimensional fluoroscopic X-ray images Ia. Furthermore, the image processor 305b is configured to set the first region A31 through the user based on the data of the three-dimensional reconstructed image 360. Accordingly, the first region A31 for the three-dimensional voxel data can be set by setting the regions A31a and A31b for at least the two images viewed in the different directions, which are obtained by cutting out the arbitrary cross-sections from the three-dimensional reconstructed image 360, respectively. Then, the first region A31 for the plurality of two-dimensional pixel data can be set by converting the three-dimensional voxel data into the plurality of two-dimensional pixel data. That is, the first region A31 can be set for many of the plurality of two-dimensional fluoroscopic X-ray images Ia used to generate the three-dimensional reconstructed image 360 simply by setting the regions A31a and A31b for at least the two images. Consequently, as compared with a case in which the first region A31 is set one by one for many of the two-dimensional fluoroscopic X-ray images Ia used to generate the reconstructed image 360, the operation load for the user to set the first region A31 can be significantly reduced or prevented.

In the third embodiment, as described above, the image processor 305b is configured to set, as the first region A31, the region in the three-dimensional reconstructed image 360 corresponding to the regions A31a and A31b set by the user in the two two-dimensional sectional images 70 viewed in the different directions, which are obtained by cutting out the arbitrary cross-sections from the three-dimensional reconstructed image 360, and set the region A31 in the plurality of two-dimensional fluoroscopic X-ray images Ia by converting the three-dimensional reconstructed image 360 in which the first region A31 has been set into the plurality of two-dimensional fluoroscopic X-ray images Ia. Accordingly, the first region A31 can be reliably set for many of the two-dimensional fluoroscopic X-ray images Ia simply by setting the regions A31a and A31b for the two images, and thus as compared with a case in which the first region A31 is set one by one for many of the two-dimensional X-ray fluoroscopic X-ray images Ia, the operation load for the user to set the first region A31 can be reliably significantly reduced or prevented.

The remaining advantages of the third embodiment are similar to those of the first embodiment.

MODIFIED EXAMPLES

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

For example, while the example in which the image processor 205b acquires the first region A21 based on the magnitude of the luminance value in the fluoroscopic X-ray image Ia has been shown in the aforementioned second embodiment, the present invention is not limited to this. In the present invention, the image processor may be configured to acquire the first region based on the magnitude of the spatial frequency in the fluoroscopic X-ray image. That is, the high spatial frequency (indicating the number of structural repetitions included in the unit length) in the image indicates that a sudden change such as an edge has occurred, and thus the image processor may determine a portion having a high spatial frequency as the first region by image analysis.

While the example in which in the X-ray imaging apparatus 300, the regions 31a and 31b are set by the user in the two two-dimensional sectional images 70 viewed in the different directions, which are obtained by cutting out the arbitrary cross-sections from the three-dimensional reconstructed image 360 has been shown in the aforementioned third embodiment, the present invention is not limited to this. In the present invention, in the X-ray imaging apparatus, regions may be set by the user in three or more two-dimensional sectional images viewed from the different directions, which are obtained by cutting out arbitrary cross-sections from the three-dimensional reconstructed image. The number of two-dimensional sectional images viewed in different directions, which is appropriate for setting regions in the fluoroscopic X-ray images as the first region, differs depending on the shape of the subject.

While the example in which the image processor 305b sets the first region A31 through the user based on the data of the three-dimensional reconstructed image 360 has been shown in the aforementioned third embodiment, the present invention is not limited to this. In the present invention, the image processor may automatically set the first region based on the data of the three-dimensional reconstructed image. In that case, as in the second embodiment, the first region may be acquired by the image process.

While the example in which the image processor 5b (205b, 305b) performs the super-resolution process by the optimization method using successive approximation calculation has been shown in each of the aforementioned first to third embodiments, the present invention is not limited to this. In the present invention, the image processor may perform the super-resolution process using a method other than the successive approximation calculation.

While the example in which the image processor 5b (205b, 305b) increases the number of pixels with respect to the second region A2 (A22, A32) of the fluoroscopic X-ray image to which the super-resolution process is not applied by the increase rate equal to the increase rate of the number of pixels due to an increase in the resolution in the first region A1 (A21, A31) by application of the super-resolution process thereto has been shown in each of the aforementioned first to third embodiments, the present invention is not limited to this. In the present invention, the number of pixels may be increased with respect to the second region by an increase rate different from the increase rate of the number of pixels due to an increase in the resolution in the first region due to application of the super-resolution process thereto.

While the example in which the image processor 5b (205b, 305b) generates the high-resolved image 50 based on four fluoroscopic X-ray images Ia (fluoroscopic X-ray images 10, 20, 30, and 40) has been shown in each of the aforementioned first to third embodiments, the present invention is not limited to this. In the present invention, a super-resolved image may be generated based on two or three fluoroscopic X-ray images, or a high-resolved image may be generated based on five or more fluoroscopic X-ray images.

While the example in which the high-resolved image 50 is generated in the X-ray imaging apparatus 100 (200, 300) that performs non-helical scan-type tomographic imaging has been shown in each of the aforementioned first to third embodiments, the present invention is not limited to this. In the present invention, the high-resolved image may be generated in an X-ray imaging apparatus that performs helical scan-type tomographic imaging.

While the example in which the high-resolved image is generated in the X-ray imaging apparatus 100 (200, 300) that performs tomographic imaging has been shown in each of the aforementioned first and second embodiments, the present invention is not limited to this. In the present invention, the high-resolved image may be generated in an X-ray imaging apparatus that does not perform tomographic imaging.

DESCRIPTION OF REFERENCE NUMERALS

1: X-ray source
2: detector
5b, 205b, 305b: image processor
50 (51, 52, 53, 54): high-resolved image
60, 360: reconstructed image
70 (70a, 70b): sectional image
90: rotation axis
100, 200, 300: X-ray imaging apparatus
A1, A21, A31: first region
A2, A22, A32: second region
E (Ea, Eb): pixel
Ic (10 (11, 12, 13, 14), 20 (21, 22, 23, 24), 30 (31, 32, 33, 34), 40 (41, 42, 43, 44)): fluoroscopic X-ray image (acquired image)
P: detection position
S: subject

The invention claimed is:

1. An X-ray imaging apparatus comprising:
an X-ray source;
a detector configured to detect X-rays radiated from the X-ray source at a plurality of detection positions translated by a movement amount smaller than a pixel size of the detector from each other; and
an image processor configured to generate a plurality of acquired images based on the X-rays detected at the plurality of detection positions, respectively, the image processor being configured to generate a high-resolved image having higher resolution than the plurality of acquired images by performing a super-resolution process to increase resolution based on the plurality of acquired images; wherein
the image processor is configured to apply the super-resolution process to a first region in each of the acquired images, the first region including a subject, and to increase a number of pixels according to an increase in resolution in the first region by application of the super-resolution process thereto by a simpler process than the super-resolution process with respect to a second region other than the first region in each of the acquired images.

2. The X-ray imaging apparatus according to claim 1, wherein the image processor is configured to increase the number of pixels by an increase rate equal to an increase rate of the number of pixels due to the increase in the resolution in the first region by the application of the super-resolution process thereto with respect to the second region in each of the acquired images to which the super-resolution process is not applied.

3. The X-ray imaging apparatus according to claim 2, wherein the image processor is configured to increase the number of pixels by the increase rate by interpolating between the pixels in the second region by an image process.

4. The X-ray imaging apparatus according to claim 1, wherein the image processor is configured to apply the super-resolution process using successive approximation calculation to the first region.

5. The X-ray imaging apparatus according to claim 1, wherein the image processor is configured to acquire the first region by an image process based on image data of the acquired images.

6. The X-ray imaging apparatus according to claim 5, wherein the image processor is configured to acquire the first region based on magnitude of a luminance value or magnitude of a spatial frequency in each of the acquired images.

7. The X-ray imaging apparatus according to claim 1, wherein
the detector is configured to detect, from a plurality of directions, the X-rays radiated from the X-ray source while rotating about a rotation axis;
the image processor is configured to generate a plurality of two-dimensional acquired images based on the X-rays detected from the plurality of directions, respectively, and to generate a three-dimensional reconstructed image obtained by reconstructing the plurality of two-dimensional acquired images; and
the first region is set by a user based on data of the three-dimensional reconstructed image.

8. The X-ray imaging apparatus according to claim 7, wherein the image processor is configured to set, as the first region, a region in the three-dimensional reconstructed image corresponding to regions set by the user in at least two two-dimensional sectional images viewed in different directions, the at least two two-dimensional sectional images being obtained by cutting out arbitrary cross-sections from the three-dimensional reconstructed image, and to set the first region in the plurality of two-dimensional acquired images by converting the three-dimensional reconstructed image in which the first region has been set into the plurality of two-dimensional acquired images.

* * * * *